(12) United States Patent
Pearce

(10) Patent No.: US 8,936,024 B2
(45) Date of Patent: Jan. 20, 2015

(54) MANUAL EMERGENCY RESUSCITATOR WITH PRE-DEFINED VOLUME CONTROL

(71) Applicant: Richard S. Pearce, Tiburon, CA (US)

(72) Inventor: Richard S. Pearce, Tiburon, CA (US)

(*) Notice: Subject to any disclaimer, the term of this patent is extended or adjusted under 35 U.S.C. 154(b) by 304 days.

(21) Appl. No.: 13/708,674

(22) Filed: Dec. 7, 2012

(65) Prior Publication Data

US 2013/0092166 A1 Apr. 18, 2013

Related U.S. Application Data

(63) Continuation-in-part of application No. 12/386,255, filed on Apr. 16, 2009, now abandoned.

(51) Int. Cl.
*A61M 16/08* (2006.01)
*A61M 16/20* (2006.01)
*A61M 16/00* (2006.01)
*A61M 16/10* (2006.01)

(52) U.S. Cl.
CPC ........... *A61M 16/20* (2013.01); *A61M 16/0075* (2013.01); *A61M 16/0084* (2013.01); *A61M 16/0078* (2013.01); *A61M 16/10* (2013.01); *A61M 2202/0208* (2013.01)
USPC ............ 128/205.14; 128/203.28; 128/204.18; 128/204.28; 128/205.13; 128/205.17

(58) Field of Classification Search
CPC ...................... A61M 16/0075; A61M 16/0078; A61M 16/0084; A61M 16/08; A61M 2205/071; A61M 2205/075; A61M 2205/078; A61H 9/005; A61H 9/0078; A61H 9/0085; A61H 9/0092; A61H 31/07; A61H 2201/0103; A61H 2201/0157; A61H 2201/1238

USPC ............ 128/204.18, 204.28, 202.28–203.11, 128/205.13–205.18; 601/23, 26, 27, 29, 601/41–44, 84, 88, 104, 105, 148–152; 602/13; 606/201, 202, 203
See application file for complete search history.

(56) References Cited

U.S. PATENT DOCUMENTS

| | | | | |
|---|---|---|---|---|
| 3,831,595 A | * | 8/1974 | Valenta et al. | 128/202.22 |
| 3,890,967 A | * | 6/1975 | Elam et al. | 128/205.17 |
| 4,297,999 A | | 11/1981 | Kitrell | |
| 4,898,167 A | | 2/1990 | Pierce et al. | |
| 5,628,305 A | * | 5/1997 | Melker | 128/202.29 |
| 5,657,751 A | * | 8/1997 | Karr, Jr. | 128/205.18 |
| 6,988,499 B2 | | 1/2006 | Holt et al. | |
| 7,284,554 B2 | * | 10/2007 | Shaw | 128/205.13 |

FOREIGN PATENT DOCUMENTS

JP 55142194 A * 11/1980

\* cited by examiner

*Primary Examiner* — Tan-Uyen (Jackie) T Ho
*Assistant Examiner* — Kathryn E Ditmer
(74) *Attorney, Agent, or Firm* — Steven A. Nielsen; Allman & Nielsen, P.C.

(57) ABSTRACT

A manual emergency resuscitator uses a volume control system having pre-defined setting to accommodate patients of different sizes. An upper plate 305 is attached to a front hinge assembly 103 and a lower housing assembly is attached to the front hinge assembly. The lower housing assembly defines the lower portions of an accordion chamber 206. A selection void 300 is defined within the upper plate 305, with the selection void further defined by voids indexed to a closed position, infant position, child position and an adult position. A volume selector cord 201 has a first end attached to a volume selector, with the volume selector contained within the selection void. Placing the volume selector into one of the predefined positions regulates the amount of air delivered by the resuscitator.

4 Claims, 4 Drawing Sheets

MANUAL EMERGENCY RESUSCITATOR WITH PRE-DEFINED VOLUME CONTROL

RELATED PATENT APPLICATION AND INCORPORATION BY REFERENCE

This is a Continuation in Part (CIP) utility patent application based upon U.S. patent application Ser. No. 12/386,255 filed on or about Apr. 16, 2009. This related application is incorporated herein by reference and made a part of this application. If any conflict arises between the disclosure of the invention in this utility application and that in the related application, the disclosure in this utility application shall govern. Moreover, the inventor incorporates herein by reference any and all patents, patent applications, and other documents hard copy or electronic, cited or referred to in this application.

BACKGROUND OF THE INVENTION (1) Field of the Invention

This invention relates generally to the field of emergency resuscitators and more specifically to manual resuscitators adaptable patients of different sizes.

(2) Description of the Related Art

Resuscitators are known by health care and emergency professionals such as medics, fire fighters, police and hospital personnel to help revive a person who has stopped breathing. Resuscitators take the place of mouth to mouth resuscitation.

One typical resuscitator is made by Ambu A/S of Ballerup, Denmark. The Ambu Spur II Resuscitator is comprised of a football shaped silicon rubber bladder having an air input aperture on one side and an air exit aperture including a tube and face mask on the opposite side. Internal check valves create an air pumping action each time the rubber bladder is squeezed thereby introducing a volume of air to the face mask and into the patient's airway.

Current resuscitator designs work relatively well and have saved countless lives; however, there is a deficiency in the prior technology. When a user squeezes the silicone rubber bladder, there is no guarantee regarding the consistency of the volume of air that is being delivered to the patient with each squeezing cycle. The volume of delivered air depends upon the force exerted upon the bladder. Furthermore, current resuscitator manufacturers have found it necessary to make three different sizes of bladder assemblies. One for infants, one for children and one for adults. This shortfall in the prior art requires an emergency vehicle has to carry three different bladder assemblies with them at any time, and finding the correct size for the situation can add additional stress to what is usually an already chaotic and stressful situation.

Another resuscitator known in the related art is U.S. Pat. No. 6,988,499 by Holt et al issued on Jan. 24, 2006. Holt discloses a resuscitator having an elongated leg member with a follower member used to adjust the volume of delivered air. By use of an elongated leg member, Holt fails to provide a compact resuscitator. Moreover, Holt's elongated leg member may become fouled or tangled during the rush and chaos of emergency use.

U.S. Pat. No. 4,297,999 issued on Nov. 3, 1981 to Kitrell discloses a complex resuscitation apparatus using a neck cushion and a spring loaded pump chamber. The unwieldy mechanical configuration of Kitrell prevents quick use in tight quarters.

U.S. Pat. No. 4,898,167 issued on Feb. 6, 1990 to Pierce et al discloses a string and ball system to adjust the height of a pump system. The string and ball system of the '167 patent creates an awkward vertical height to the apparatus and prevents quick one handed volume adjustments.

BRIEF SUMMARY OF THE INVENTION

An object of the invention is to provide a resuscitator that allows the user to deliver a precise volume of air to ventilate a patient no matter what hand size or hand strength the rescuer may possess.

Another object of the invention is to provide a resuscitator with an adjustable volume stroke to accommodate an infant, a child or an adult.

Another object of the invention is to provide one handed adjustments to control the volume of air delivered.

Disclosed embodiments include the use of preset indexed

Other objects and advantages of the present invention will become apparent from the following descriptions, taken in connection with the accompanying drawings, wherein, by way of illustration and example, an embodiment of the present invention is disclosed.

DETAILED DESCRIPTION OF THE PREFERRED EMBODIMENTS

Figure 1:
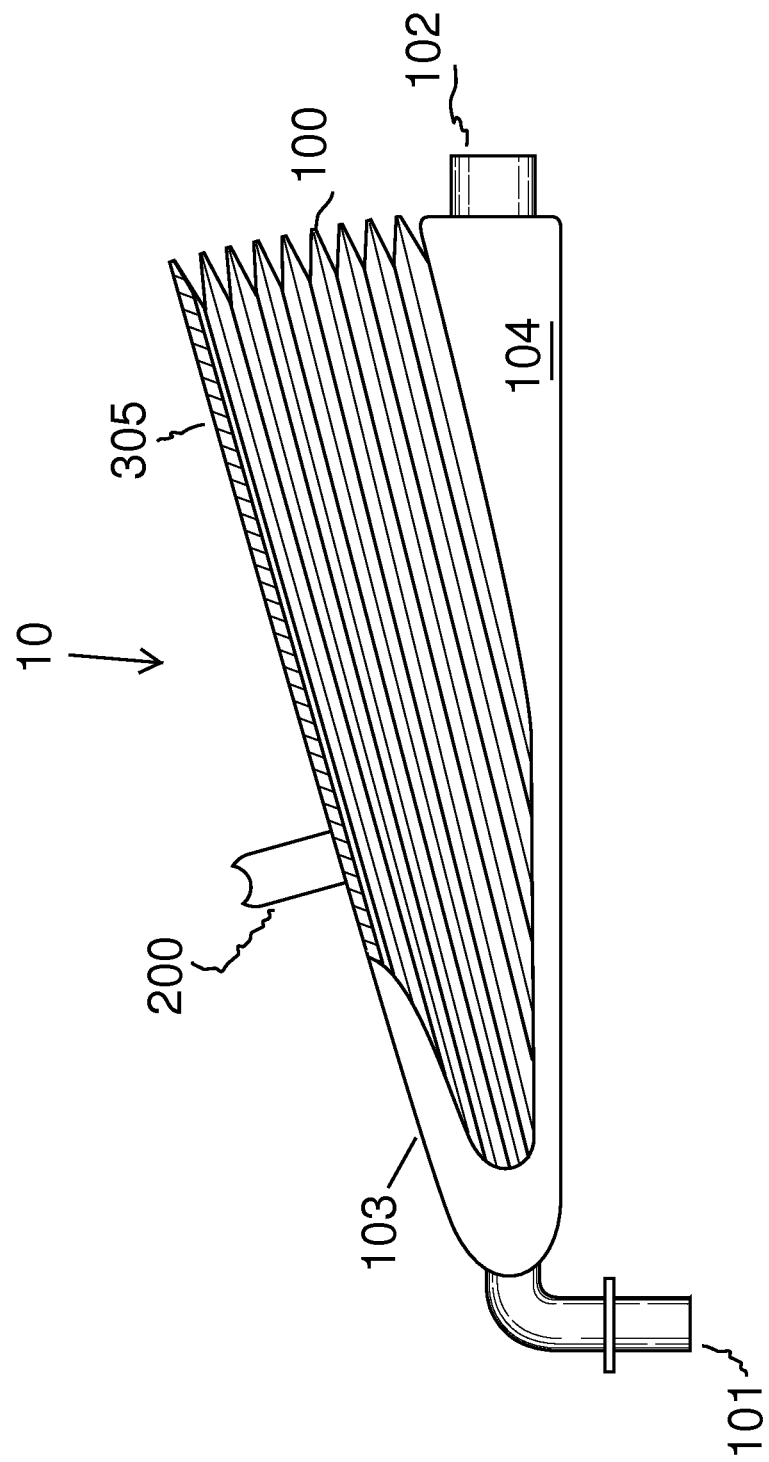
FIG. 1 is a side view of one embodiment of the invention.

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

REFERENCE NUMBERS 10 a disclosed embodiment in general
100 accordion section
101 air exit value
102 oxygen input value
103 front hinge assembly
104 lower housing assembly
200 volume selector
201 volume selector cord
202 first cord pivot pin
203 second cord pivot pin
204 third cord pivot pin
205 cord anchor
206 accordion chamber
207 index pin of volume selector 200
300 selection void defined by an upper plate
301 closed position
302 infant position
303 child position
304 adult position
305 upper plate which comprises the selection void 300
306 bottom side of upper plate 305
400 optional oxygen bag
401 tube to optional oxygen bag 400

Referring to FIG. 1, one embodiment of the invention is shown in general 10 wherein a lower housing assembly 104 supports an accordion section 100. The lower housing assembly 104 is attached to an oxygen input value 102 and front hinge assembly 103. An oxygen input value 101 attaches to the front hinge assembly 103. A volume selector 200 sits on top of the accordion section 100. An upper plate 305 is attached to the font hinge assembly 103. The details of the upper plate are shown in more detail in FIG. 3.

Figure 2:
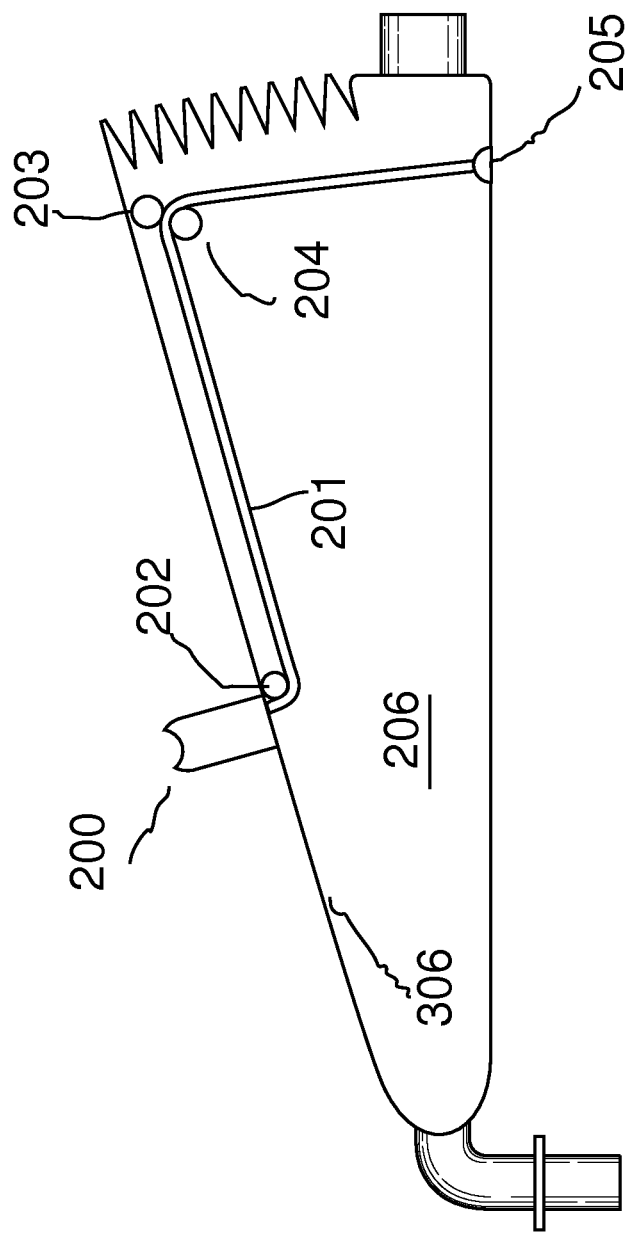
FIG. 2 is a side sectional view of one embodiment of the invention.

FIG. 2, depicts a side sectional view showing the volume selector 200 connected to a volume selector cord 201. A first cord pivot pin 202, second cord pivot pin 203 and third cord pivot pin 204 contain the volume selector cord 201. As shown, as the volume selector 200 is moved the size of the accordion chamber 206 is made larger or smaller. The second cord pivot pin 203 and the third cord pivot pin 204 are positioned adjacent to one another and on opposite sides of the volume selector cord 201.

Figure 3:
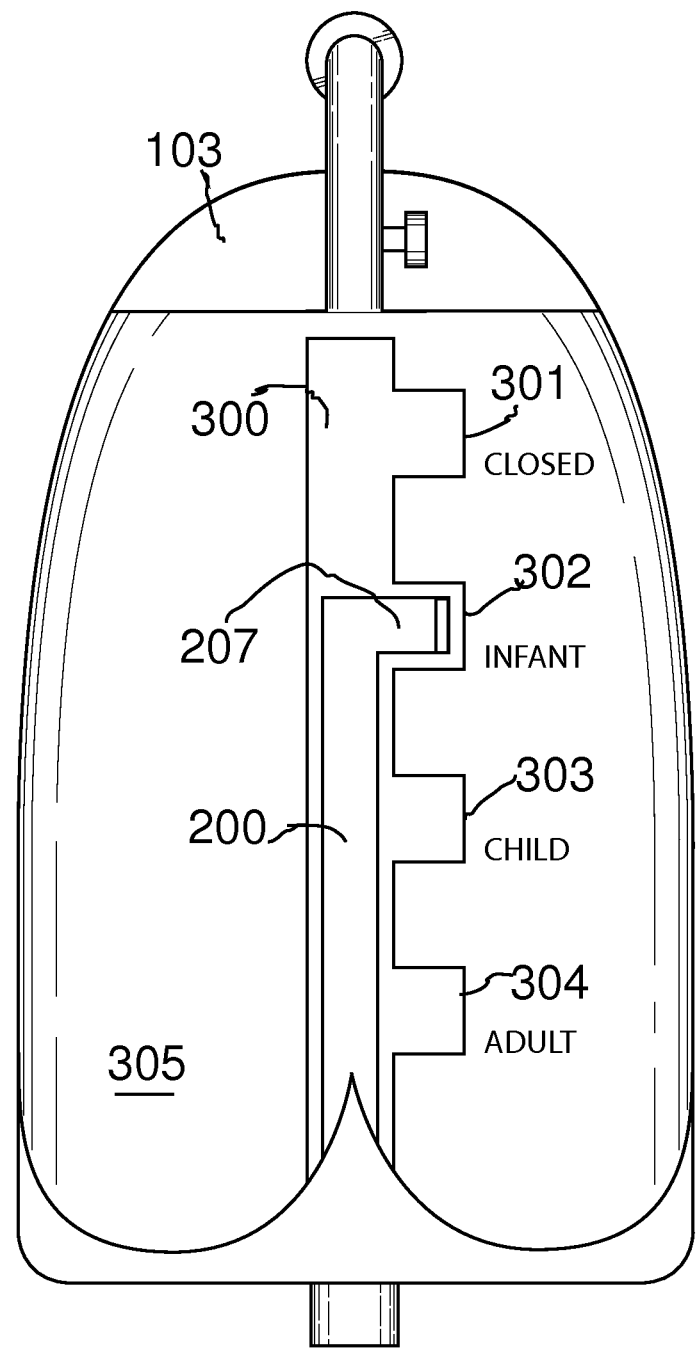
FIG. 3 is a top plan view of one embodiment of the invention.

FIG. 3 shows a top view exposing a selection void 300 wherein the volume selector 200 may travel to adjust the volume of the accordion chamber. In order to deliver the correct amount of air, positions for infant 302, child 303 and adult 304 are provided. A closed position 301 allows for compact storage of the device. The volume selector 200 may comprise an index pin 207, the index pin fitting into the closed, infant, child or adult positions. The selection void 300 is defined by an upper plate 305. The upper plate 305 is attached to the front hinge assembly 103. The front hinge assembly 103 is attached to the lower housing assembly 104, as shown in FIG. 1. The volume selector may rotate such that the index pin moves from a vertical position for fore and aft movement and then rotates to mate into the closed, infant, child or adult position.

Figure 4:
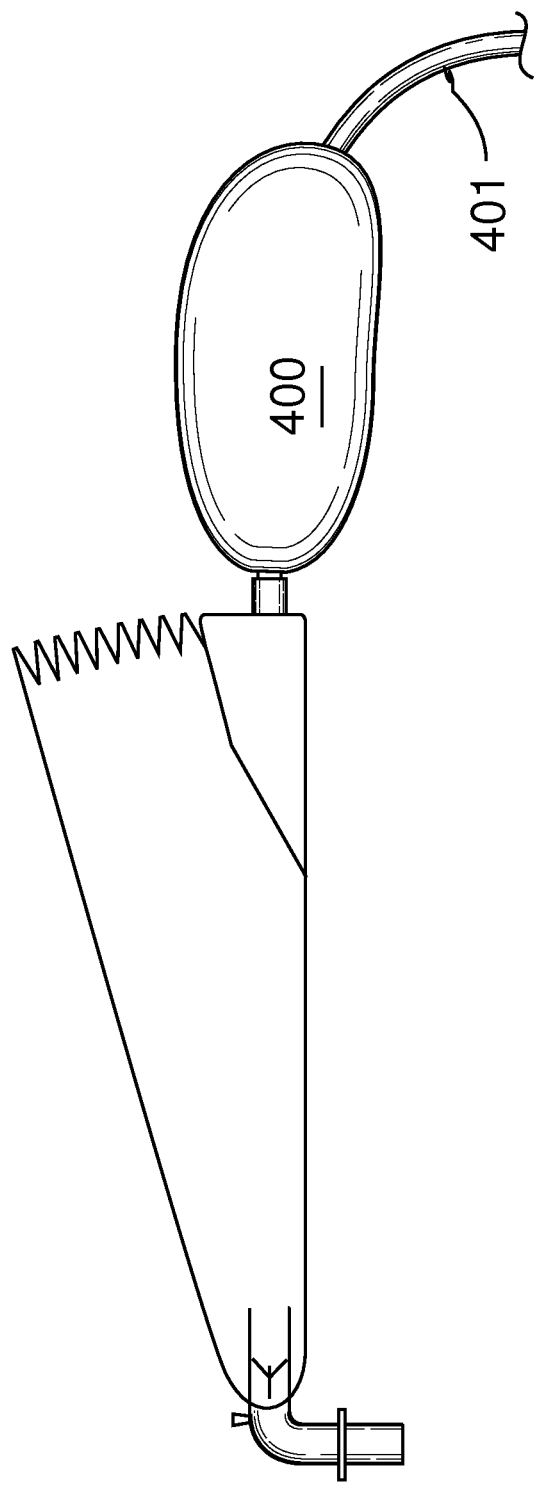
FIG. 4 is a side view of one embodiment of the invention.

FIG. 4 shows an alternative configuration with an oxygen bag 400 fed by a tube 401. Under some circumstances, the use of axillary oxygen is helpful.

The above described and illustrated invention allows a user such as a paramedic to be ready to resuscitate an individual no matter what their lung capacity because the invention can be quickly set so that the air delivered to the patient is ideal and consistent for the lung size of the individual.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

Items. Disclosed embodiments include the following items.

1. A resuscitation apparatus comprising:
a) a lower housing assembly 104 attached to an oxygen input valve 102,
b) an accordion section 100 attached to the lower housing assembly 104,
c) a front hinge assembly 103 attached to the lower housing assembly 104,
d) an upper plate 103 attached to the lower housing assembly 104,
e) the upper plate defining a sectional void 300, the sectional void 300 further defined by a closed position void 301, an infant position void 302, a child position void 303 and an adult position void 304;
f) a volume selector 200 contained within the sectional void 300, the volume selector 200 comprising an index pin 207, the index pin 207 configured to mate into the closed position void 301, the infant position void 302, the child position void 303 and the adult position void 304;
g) a cord 201 having a first end attached to the volume selector and the cord having a second end attached to a cord anchor 205, the cord anchor attached to the lower housing assembly 104;
h) the upper plate 305 having a bottom side 306, the bottom side attached to a first cord pivot pin 202, a second cord pivot pin 203 and a third cord pivot pin 204, the volume selector cord 201 deflected by the first cord pivot pin 202 and the volume selector cord 201 contained between the second cord pivot pin 203 and the third cord pivot pin 204.

2. A method of using the resuscitation apparatus of item 1, the method comprising the steps of:
a) adjusting the volume of the accordion section 100 by moving the volume selector 200 an available position, the available position selected from the group comprising the closed position void, the infant position void 302, the child position void 303 and the adult position void 304.

3. The method of item 2 further comprising the step of inserting the index pin 207 of the volume selector into an available position.

4. A resuscitation kit, the kit comprising:
a) a lower housing assembly 104 attached to an oxygen input valve 102,
b) an accordion section 100 attached to the lower housing assembly 104,
c) a front hinge assembly 103 attached to the lower housing assembly 104,
d) an upper plate 103 attached to the lower housing assembly 104,
e) the upper plate defining a sectional void 300, the sectional void 300 further defined by a closed position void 301, an infant position void 302, a child position void 303 and an adult position void 304;
f) a volume selector 200 contained within the sectional void 300, the volume selector 200 comprising an index pin 207, the index pin 207 configured to mate into the closed position void 301, the infant position void 302, the child position void 303 and the adult position void 304;
g) a cord 201 having a first end attached to the volume selector and the cord having a second end attached to a cord anchor 205, the cord anchor attached to the lower housing assembly 104;
h) the upper plate 305 having a bottom side 306, the bottom side attached to a first cord pivot pin 202, a second cord pivot pin 203 and a third cord pivot pin, the volume selector cord 201 deflected by the first cord pivot pin 202 and the volume selector cord 201 contained between the second cord pivot pin 203 and the third cord pivot pin.

5. The kit further comprising an oxygen bag 400 and a tube 401.

What is claimed is:

1. A resuscitation apparatus comprising:
a) a lower housing assembly attached to an oxygen input valve;
b) an accordion section attached to the lower housing assembly;
c) a front hinge assembly attached to the lower housing assembly;
d) an upper plate attached to the lower housing assembly;
e) the upper plate defining a sectional void, the sectional void further defined by a closed position void, an infant position void, a child position void and an adult position void;
f) a volume selector contained within the sectional void, the volume selector comprising an index pin, the index pin configured to mate into the closed position void, the infant position void, the child position void and the adult position void;

g) a volume selector cord having a first end attached to the volume selector and the volume selector cord having a second end attached to a cord anchor, the cord anchor attached to the lower housing assembly; and h) the upper plate having a bottom side, the bottom side attached to a first cord pivot pin, a second cord pivot pin and a third cord pivot pin, the volume selector cord deflected by the first cord pivot pin and the volume selector cord contained between the second cord pivot pin and the third cord pivot pin.

2. A method of using the resuscitation apparatus of claim 1, the method comprising the steps of:

adjusting the volume of the accordion section by moving the volume selector an available position, the available position selected from the group comprising the closed position void, the infant position void, the child position void and the adult position void.

3. The method of claim 2 further comprising the step of inserting the index pin of the volume selector into an available position by moving the volume selector fore and aft and by rotating the index pin to mate into an available position.

4. A resuscitation kit, the kit comprising:

an oxygen bag; a tube; and a resuscitation apparatus, the resuscitation apparatus comprising:

a) a lower housing assembly attached to an oxygen input valve;

b) an accordion section attached to the lower housing assembly;

c) a front hinge assembly attached to the lower housing assembly;

d) an upper plate attached to the lower housing assembly;

e) the upper plate defining a sectional void, the sectional void further defined by a closed position void, an infant position void, a child position void and an adult position void;

f) a volume selector contained within the sectional void, the volume selector comprising an index pin, the index pin configured to mate into the closed position void, the infant position void, the child position void and the adult position;

g) a cord having a first end attached to the volume selector and the cord having a second end attached to a cord anchor, the cord anchor attached to the lower housing assembly; and h) the upper plate having a bottom side, the bottom side attached to a first cord pivot pin, a second cord pivot pin and a third cord pivot pin, the volume selector cord deflected by the first cord pivot pin and the volume selector cord contained between the second cord pivot pin and the third cord pivot pin.

* * * * *